United States Patent
Zeqiri

(10) Patent No.: US 8,619,494 B2
(45) Date of Patent: Dec. 31, 2013

(54) IMAGING APPARATUS AND METHOD

(75) Inventor: Bajram Zeqiri, Teddington (GB)

(73) Assignee: The Secretary of State for Innovation, Universities and Skills, London (GB)

(*) Notice: Subject to any disclaimer, the term of this patent is extended or adjusted under 35 U.S.C. 154(b) by 129 days.

(21) Appl. No.: 13/145,260

(22) PCT Filed: Jan. 21, 2010

(86) PCT No.: PCT/GB2010/000095
§ 371 (c)(1),
(2), (4) Date: Sep. 20, 2011

(87) PCT Pub. No.: WO2010/084319
PCT Pub. Date: Jul. 29, 2010

(65) Prior Publication Data
US 2012/0010510 A1   Jan. 12, 2012

(30) Foreign Application Priority Data
Jan. 21, 2009 (GB) .................... 0901022.4

(51) Int. Cl.
*G03B 42/06* (2006.01)
*A61B 8/00* (2006.01)
*G01H 3/12* (2006.01)

(52) U.S. Cl.
CPC . *G01H 3/125* (2013.01); *A61B 8/00* (2013.01)
USPC ................. 367/7; 600/437; 600/459

(58) Field of Classification Search
USPC ...................... 367/7; 600/437, 459
See application file for complete search history.

(56) References Cited

U.S. PATENT DOCUMENTS 3,774,043 A * 11/1973 Le Carvennec ............... 250/330
3,982,068 A    9/1976 Charles et al.
(Continued)

FOREIGN PATENT DOCUMENTS

| JP | 8178748 | 7/1996 |
|---|---|---|
| WO | 03044473 | 5/2003 |
| WO | 2009004558 | 1/2009 |

OTHER PUBLICATIONS

Fay, et al. (1994) "Thermoacoustic Senor for Ultrasound Power Measurements and Ultrasonic Equipment Calibration" Ultrasound Med. Biol. 20(4):367-373.
Zeqiri & Barrie (2008) "Evaluation of a Novel Solid-State Method for Determining the Acoustic Power Generated by Physiotherapy Ultrasound Transducers" Ultrasound Med. Biol. 34(9):1513-1527.

(Continued)

*Primary Examiner* — Isam Alsomiri
*Assistant Examiner* — James Hulka
(74) *Attorney, Agent, or Firm* — Edward J. Baba; Bozicevic, Field & Francis LLP

(57) ABSTRACT

A system (100) uses a pyroelectric membrane (122) and an ultrasound absorber (123) to measure the amount of ultrasonic energy received from a transmitter (105) through a sample (110). The thermal response of the pyroelectric membrane (122) is sensitive to ultrasound time-averaged intensity but is insensitive to the phase of the ultrasound. A waveform (200) shows rising (210), peak (220) and decaying (230) portions of a signal from the pyroelectric membrane (122) in response to on/off transitions of the transmitter (105). A system (300) uses a peak detector (333) to automatically turn the transmitter (105) on/off. A system (400) has background removal circuitry (444) to remove unwanted accelerometer-induced noise or electrical noise. A multi-element ultrasonic sensor (520) has cavities (555) so that a dummy sensor (521 b) can be used to compensate for unwanted accelerometer sensitivity of a sensor element (521 a). A sensor (620) has ultrasound absorbing (or reflective) regions (660) to compensate for unwanted accelerometer sensitivity. A system (900) has a low frequency path (909) sensitive to the pyroelectric effect, and a high frequency path (919) sensitive to the acoustic pressure amplitude, of a signal from a sensor (920). A sensor (1020) uses a pyroelectric material (1022) with poled regions (1099) separated by a non-poled region (1098).

48 Claims, 11 Drawing Sheets

(56) References Cited

U.S. PATENT DOCUMENTS 5,638,822 A * 6/1997 Seyed-Bolorforosh et al. ............... 600/459
2006/0032312 A1 * 2/2006 Auner et al. ................... 73/570
2006/0116579 A1 6/2006 Li et al.

OTHER PUBLICATIONS

Zeqiri, et al. (2007) "A Novel Pyroelectric Method of Determining Ultrasonic Transducer Output Power: Device Concept, Modeling and Preliminary Studies" IEEE Trans, Ultrason. Ferroelectr. Freq. Control 54(11):2318-2330.

* cited by examiner

IMAGING APPARATUS AND METHOD

The present invention relates to a imaging apparatus and a method, system for measuring a property of a sample, as well as to an ultrasonic receiver. In particular, but not exclusively, the preferred embodiments described herein relate to ultrasound imaging by measuring the spatial distribution of ultrasonic absorption of a sample and to phase insensitive ultrasound imaging. The preferred embodiments relate to medical imaging.

Typical ultrasound medical imaging devices use transducers which are made from piezoelectric materials. A single transducer can be operated in pulse-echo mode, to image low-level acoustic reflections or scattering from tissues, or through-transmission, using a second transducer to detect the acoustic signal passing through a sample. The electrical output of the transducer is said to be phase-sensitive, as it is able to differentiate the compressional and rarefactive half-cycles of the acoustic wave. Typically, an array of these phase sensitive transducer elements may be used to deduce the spatial arrangement of body tissue between an ultrasonic energy source and the transducer array used to detect the transmitted ultrasound. This can be carried out through implementing 2-D or 3-D tomographic reconstruction techniques. It is well established that the accuracy of these images generated can be degraded by refraction and reflection of the acoustic wave at interfaces between different tissue elements. Also, as the output of the receiving transducer depends on the pressure averaged across its surface, images can be susceptible to phase-cancellation artefacts, due to different phases of the acoustic signals arriving at the transducer. This arises as the different constituents of the tissue possess slightly different speeds of sound. A feature of phase sensitive detectors is that they typically require complicated and expensive signal conditioning circuitry such as frequency mixers and demodulators.

WO 03/044473 discloses an ultrasonic power meter for measuring ultrasonic power emitted by a device under test. The meter includes a casing forming a chamber within which an ultrasonic absorber formed from polyurethane material is located. Overlying the absorber is a membrane of polyvinylidene fluoride which acts as a pyroelectric detector. The meter also includes a transfer medium, typically water, for allowing the transfer of ultrasonic energy emitted from a device under test to the meter. The sensor disclosed in WO 03/044473 may be used in some embodiments of the apparatus disclosed herein.

"A Novel Pyroelectric Method of Determining Ultrasonic Transducer Output Power: Device Concept, Modeling, and Preliminary Studies"; IEEE Transactions on Ultrasonics, Ferroelectrics, and Frequency Control, vol. 54, no. 11, November 2007; discloses a thermally based method of monitoring acoustic output power generated by ultrasonic transducers. It exploits the pyroelectric properties of a thin membrane of polyvinylidene fluoride (PVDF). The membrane is backed by a thick layer of polyurethane rubber that is extremely attenuating to ultrasound, with the result that the majority of the applied acoustic power is absorbed within a few millimetres of the membrane-backing interface. Through the resultant rapid increase in temperature of the membrane, a voltage is generated across its electrodes whose magnitude is proportional to the rate of change of temperature with respect to time. The sensor design disclosed in this paper may be used in the apparatus of some embodiments disclosed herein.

The present invention seeks to provide improved imaging of a sample, for instance a patient, an improved system for measuring intrinsic properties of a sample, an improved system for measuring ultrasound transmitted through said sample and an improved ultrasonic receiver. In particular, the preferred embodiments disclosed herein are directed to medical imaging able to provide a reliable image of tissue for use, for example, in the detection of abnormal growths in tissue, particularly cancerous growths, without exhibiting some of the disadvantages of existing imaging technologies.

According to an aspect of the present invention, there is provided imaging apparatus, comprising: at least one ultrasonic transmitter operable to ensure coverage of an ultrasonic beam across an imaging area; at least one ultrasonic receiver, wherein the or each ultrasonic receiver is sensitive to intensity of an ultrasonic field generated by the transmitter or transmitters; wherein the or at least one of said ultrasonic receivers is arranged to sense the ultrasonic field in a part of the imaging area; and signal processing circuitry operable to process a signal from the or each ultrasonic receiver to derive therefrom an intensity measure across said imaging area.

The apparatus is preferably medical imaging apparatus.

An advantage of some aspects and embodiments of the present invention is that they are sensitive to the intensity of ultrasound and insensitive to phase. Known ultrasound imaging devices (e.g. for medical ultrasonography) are sensitive to the phase and thus images produced by phase sensitive devices are degraded due to inhomogeneities in the tissue path, which have differing acoustic properties such speed of sound, absorption and density. Effects such as refraction, reflection, diffraction, can lead to waveform and wave front aberrations. Known ultrasound imaging devices typically require post processing of the signals to improve image quality, by reducing the sensitivity to phase aberrations. In contrast, some embodiments of the present invention measure the distribution of time-averaged ultrasonic intensity transmitted through an interrogated sample volume, with the aim of providing a more accurate spatial map of the ultrasonic absorbing properties of the sample being measured.

Embodiments of the present invention may be used to measure the properties of human tissue, for example during mammography, through 3-D tomographic reconstruction methods, or animal tissue, or it may be used to detect defects, for example cracks or weld defects, in engineering components. Thus, there is disclosed herein a system and method of phase insensitive ultrasound imaging. This can be particularly advantageous given that tissue is inhomogeneous, which leads to aberrations in phase sensitive systems as a result of the changes in speed of sound of an ultrasonic wave through the tissue. The preferred embodiments can provide a "point" measurement, that is using a sensor as small as possible, in one example having a nominal diameter of less than 2 mm, preferably less than 1 or 0.5 mm and in one example of around 0.4 mm. Such a sensor responds to intensity in contrast to existing sensor technologies which respond to pressure. In practice, such small sensors will provide a response to the field intensity which is averaged across the detector area.

It is envisaged that practical applications of the technology taught herein can be used to form a 2-D (or 3-D) array of transducers (receivers) that will allow the imaging of an ultrasound beam once it has passed through tissue, to detect changes in pathology. Existing transducers for medical ultrasound scanning are formed of phase sensitive piezo-elements and it is accepted that such images are degraded by such phase sensitivity, due to inhomogeneities in the tissue path, diffraction and waveform aberrations. Indeed, in many approaches post processing of the signals is necessary in order to attempt to reduce the sensitivity to phase and improve image quality and thus enhance clinical diagnosis. A 2-D intensity sensitive array along the lines taught herein can be much less sensitive to such effects.

In the preferred embodiments a frequency of 0.5 to 3 MHz is chosen for imaging. This is much lower than conventional imaging systems. Advantageously, beam energy is provided by generating the field in long bursts, for instance, for times exceeding a hundred cycles at the frequency of interest. It is preferred that the field has a time averaged intensity of around 3 watts/cm$^2$ or less, although this could be in the range form 50 mW/cm$^2$ to 10 w/cm$^2$, more preferably from 1 w/cm$^2$ to 5 W/cm$^2$.

According to another aspect of the present invention, there is provided a system for measuring a property of a sample, comprising: an ultrasonic transmitter; an ultrasonic receiver, wherein the ultrasonic receiver is sensitive to the time-averaged intensity of the ultrasonic field; a positioner for positioning a sample in a path between the ultrasonic transmitter and the ultrasonic receiver; and signal processing circuitry for processing a signal from the ultrasonic receiver.

According to another aspect of the present invention, there is provided a system for measuring a property of a sample, comprising: an ultrasonic transmitter; an ultrasonic receiver, wherein the ultrasonic receiver is sensitive to the time-averaged intensity of ultrasonic energy; and signal processing circuitry for processing a signal from the ultrasonic receiver, wherein the signal processing circuitry is operable to measure one or more first features at a first time and to measure one or more second features at a second, subsequent, time.

According to another aspect of the present invention, there is provided a system for measuring a property of a sample, comprising: an ultrasonic transmitter; an ultrasonic receiver, wherein the ultrasonic receiver is sensitive to the intensity of ultrasonic energy; and signal processing circuitry for processing a signal from the ultrasonic receiver, wherein the signal processing circuitry comprises a detector operable to detect features in the signal and modulate the ultrasonic transmitter in response to the features.

According to another aspect of the present invention, there is provided an ultrasonic receiver comprising: an ultrasonic absorber; a pyroelectric ultrasonic sensing element in thermal communication with the ultrasonic absorber; a pyroelectric compensation element substantially thermally isolated form the ultrasonic absorber.

Embodiments of the present invention are described below, by way of example only, with reference to the accompanying drawings, in which.

Figure 1:
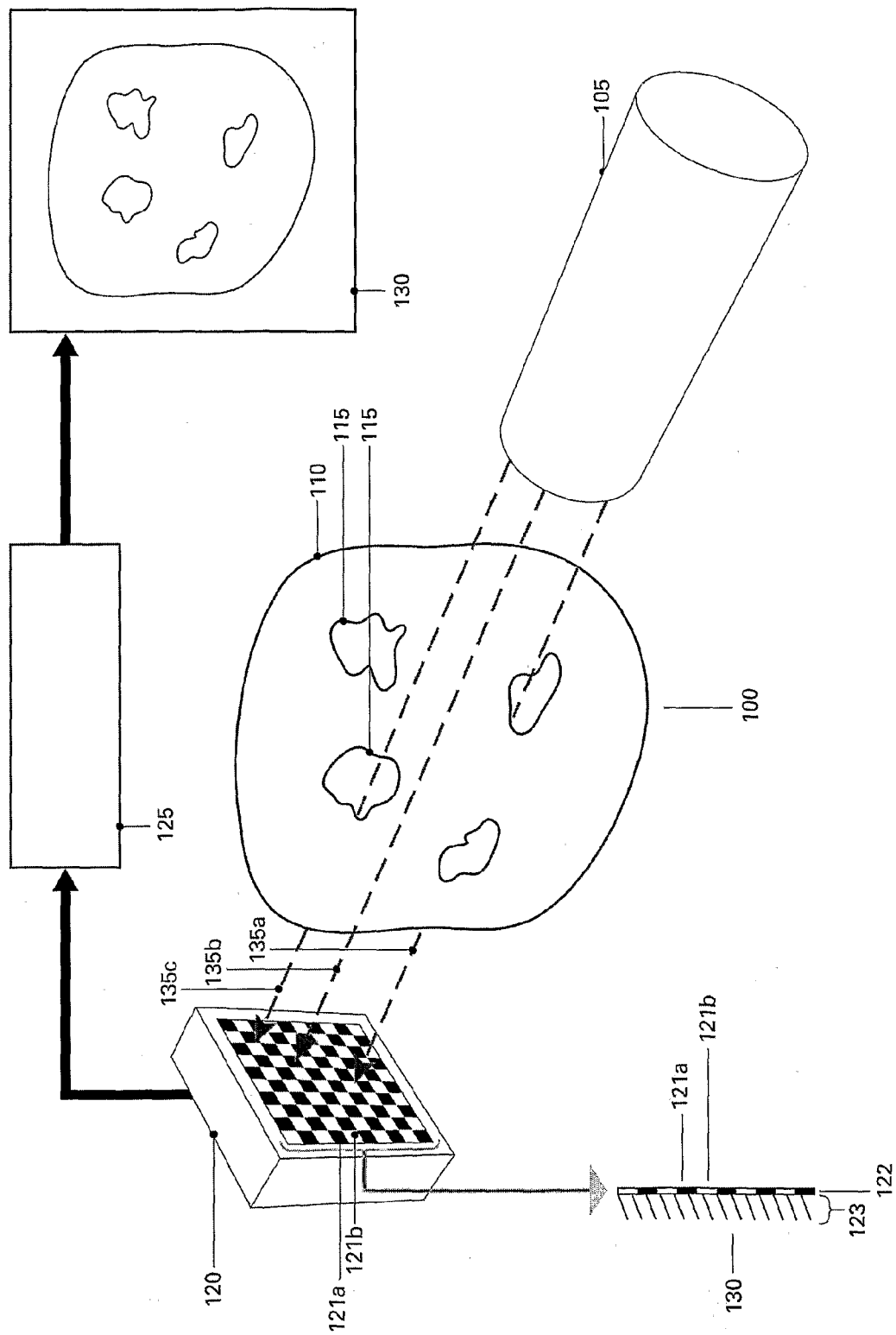
FIG. 1 shows an ultrasonic imaging system.

FIG. 1 shows an ultrasonic imaging system 100. The system 100 comprises an ultrasound transmitter 105 for emitting ultrasound energy which passes through a sample 110 to an ultrasonic receiver array 120. The ultrasonic receiver array 120 comprises a plurality of ultrasonic receiver elements 121a, 121b. The elements could be made from a single sheet of sensor material or may be formed by a laminate of a plurality of membranes. A 2-D array may be formed on one of these membranes or it may be built up of a number of discrete and independent elements held to together to form the 2-D matrix. It may be flat, or may be shaped appropriately for the sample being tested.

In FIG. 1 the ultrasonic receiver array 120 is, in this embodiment, a 10×10 array of ultrasonic receiver elements 121a, 121b. The lower left portion of FIG. 1 shows a cross-sectional view through the ultrasonic receiver array 120. The ultrasonic receiver array 120 comprises a temperature sensitive layer 122 that overlies an ultrasound absorber 123. In FIG. 1 the temperature sensitive layer 122 comprises discrete pyroelectric elements, such as PVDF (polyvinylidene fluoride). In other embodiments the layer 122 could be formed of or include other materials such as piezo-composites; mixtures of ceramics and polymers, which may have superior features in terms of sensitivity. PVDF is relatively cheap and readily available in suitable form for this application. In some embodiments the temperature sensitive layer 122 may comprise temperature sensors such as thermocouples, thermistors and/or temperature-monitoring diodes (PN junctions), disposed in such as way as to measure the time-dependent temperature at the surface of the ultrasound absorber 123.

FIG. 1 shows that the ultrasonic absorber 123 is provided in the form of a layer behind (from the point of view of ultrasonic energy emitted from the ultrasound transmitter 105) the temperature sensitive layer 122. The ultrasonic absorber 123 absorbs incident ultrasonic energy, preferably with an attenuation such that incident ultrasonic energy is substantially completely absorbed within the ultrasonic absorber 123 within a thickness of a few wavelengths of the ultrasonic frequency (ultrasound can be used at frequencies of 20 kHz and above, though it is more typical to use ultrasound having a frequency up to 10 MHz, although a frequency of a few MHz to a few tens of MHz could also be used. The chosen frequency will depend on the acoustic properties of the sample being imaged, with the requirement that the absorption needs to be low enough to ensure sufficient energy is transmitted through to generate an image. Tissue absorption, for example, increases almost linearly with frequency. As high a frequency as possible should be used, to increase acoustic contrast between adjacent tissues, and to improve spatial resolution.

The temperature sensitive layer 122 is preferably sufficiently thin so that substantially all the incident ultrasonic energy passes through the temperature sensitive layer 122 and is absorbed by the ultrasonic absorber 123. The ultrasound energy increases the temperature of the ultrasonic absorber 123 (more accurately, the ultrasound energy increases the temperature of the face of the ultrasonic absorber 123 that is in contact with the temperature sensitive layer 122) and this temperature rise is detected by the temperature sensitive layer 122.

The temperature sensitive layer 122 may be of a thickness comparable with the wavelength of the ultrasound. More preferably, the temperature sensitive layer 122 will be thinner than the wavelength of the ultrasound, to reduce reflections. For example, ultrasound of a frequency of 1 MHz has a wavelength in water of about 1.5 mm. If PVDF film is used for the temperature sensitive layer 122, the PVDF film may have a thickness of 50 μm and the ultrasonic absorber 123 may have a thickness of 10 mm. Polyurethane rubber with small inclusions of air, e.g. 10-20 μm diameter bubbles, to boost the acoustic absorption in the material, may be used for the ultrasonic absorber 123. Other materials may be added to this backing material to optimise its properties, either acoustic or thermal. Electrical signals from the ultrasonic receiver array 120 are conditioned by signal processing circuitry 125. As those skilled in the art will appreciate, such circuitry may comprise voltage amplifiers, charge amplifiers, filters (such as low pass, high pass or band pass), and analogue to digital converters (ADCs). Data that represents the sample 110 may then be displayed on a display device 130 to provide a two dimensional map of how the attenuation of the sample 110 varies across the sample 110. If the system 100 is rotated or translated relative to the sample 100 and many measurements are made sufficient to implement tomographic reconstruction, then the display device 130 may be used to display a three dimensional map of how the attenuation of the sample 110 varies through the sample 110.

Pyroelectric materials tend also to be piezoelectric. Thus the ultrasonic receiver elements 121 will produce a signal, when for example using ultrasound of 1 MHz, in the MHz range, due to the piezoelectric effect, in response to the pressure of the ultrasound. This MHz range signal is sensitive to the phase of the ultrasound. The ultrasonic receiver elements 121 will also produce a signal, at a much lower frequency, due to the pyroelectric effect.

The pyroelectric effect can generate electrical charge in proportion to the rate of change of temperature of the pyroelectric elements 121, dependent on the electrical impedance of the measurement instrumentation to which the sensor is attached. As the duration of ultrasound from the ultrasound transmitter 105 continues, thermal conduction across the pyroelectric elements 121, or into the water, will lead to a gradual lessening in the rate of heating of the ultrasonic absorber 123 (more accurately, there will be a reduction in the rate of temperature increase of the surface of the ultrasonic absorber 123 that is in contact with the temperature sensitive layer 122) and will gradually warm the sample 110 (or medium such as water) so that thermal equilibrium is approached. Depending on the sensor dimensions and its electrical properties such as capacitance, and the heat capacity of the constituent material, along with the impedance of the attached electronic instrumentation such as the amplifier, the thermal time constant of the elements 121 will typically be of the order of milliseconds, for example 50 ms. Thus, a low pass filter can be used, if necessary, to filter out the MHz piezoelectric signal but to pass the Hz-to-kHz range pyroelectric signal.

The system 100 may be used to detect inhomogeneities in the tissue sample, for example, cancerous regions or cysts 115 in the sample 110.

When the ultrasound transmitter 105 is initially turned on, ultrasound energy will pass through the sample 110 and will be received by the ultrasonic receiver array 120. This will provide a snap-shot of the spatial distribution of acoustic intensity transmitted through the tissue sample. The intensity at any point will depend on the tissue path taken by the acoustic wave fronts, and this will in turn depend on the tissue structure. Some ultrasonic receiver elements 121 of the array will, in effect, be partially obscured by the cancerous regions 115 (that is, for cancers where the disease makes the cancerous regions 115 more absorbing of ultrasonic energy than normal regions of tissue) and less ultrasonic energy will be received by these elements 121 compared to other elements of the array. The ultrasound energy is absorbed by the ultrasonic absorber 123; each ultrasonic receiver element 121 of the 10×10 ultrasonic receiver array 120 measures the temperature rise of a respective portion of ultrasonic absorber 123. It is to be appreciated cancerous tissue can either be more or less absorbing than normal tissue, thus the image transmitted depends on the acoustic contrast with adjacent tissue.

FIG. 1 shows paths 135a, 135b, 135c. Paths 135a, 135c encounter cancerous regions 115. Path 135b passes only through normal tissue. Thus, the ultrasonic receiver elements 121 that correspond to paths 135a, 135c receive less ultrasonic energy than the ultrasonic receiver element 121 that corresponds with path 135b.

The sample 110 may be held by clamps to prevent movement. Where the sample 110 comprises mammary tissue, the sample 110 may be held in a machine similar to mammography machine (shown in FIG. 11 and described in more detail below). This may involve the patient lying face downwards on a couch with their breast(s) positioned within a central water-filled reservoir, around the walls of which are positioned the ultrasonic receiver and transmitter which can be scanned around the breast to acquire the data required for 3-D tomographic reconstruction.

A transfer fluid such as water may be used to improve the coupling of ultrasonic energy from the ultrasonic transmitter 105 to the sample 110, and/or to improve the coupling from the sample 110 to the ultrasonic receiver array 120. The properties of the water couplant medium may be modified to improve the images generated, for example through the addition of cavitation inhibitors or solutes which match the speed of sound to that of breast tissue.

In other applications, the sample 110 may comprise a food product, for example soup, and the system 100 may be used to detect foreign objects, for example glass or metal, in the soup. In such applications, the sample 110 may be pumped through a pipe (not shown) past an ultrasonic transmitter 105 and an ultrasonic receiver 120. The pipe may be plastic (compared to metal or glass) to improve the coupling of ultrasound through the wall of the pipe.

FIG. 1 shows a system 100 having a single ultrasound transmitter 105 and an ultrasonic receiver array 120 comprising a 10×10 array of elements 121. In other arrangements, the ultrasonic receiver array 120 may have more or fewer elements 121. The minimum number is a single element 121. In other arrangements, the system 100 may have two or more ultrasonic transmitters. For example, the ultrasonic transmitter may comprises two or more elements. Where two or more ultrasonic transmitters are used, they may form part of a phased array to direct a wave front towards the ultrasonic receiver array 120. Additionally, the transmitter elements may be able to transmit ultrasound at two or more frequencies, either by having a single transducer able to be driven over a range of frequencies, or by interspersing different transducers capably of generating sound at (say) 1 and 3 MHz within the transmitter array. In embodiments having a single transmitter 105 and a single receiver element 121 and for multiple receive/transmit arrays, the transmitter 105 and the receiver element 121 may be moved relative to each other to scan a sample 110. Alternatively or additionally, the sample 110 may be moved relative to the transmitter and/or the receiver element 121.

The ultrasonic receiver array 120 may in some arrangements be provided with integrated signal processing circuitry 125. The signal processing circuitry 125 may be for example mounted close to the temperature sensitive layer 122 or to the ultrasound absorbing layer 123. Such integration has the advantage of reducing the length of wiring between the ultrasonic receiver elements 121 and the signal processing circuitry 125; the length reduction can reduce stray capacitance and/or reduce sensitivity to external electrical interference.

Figure 2:
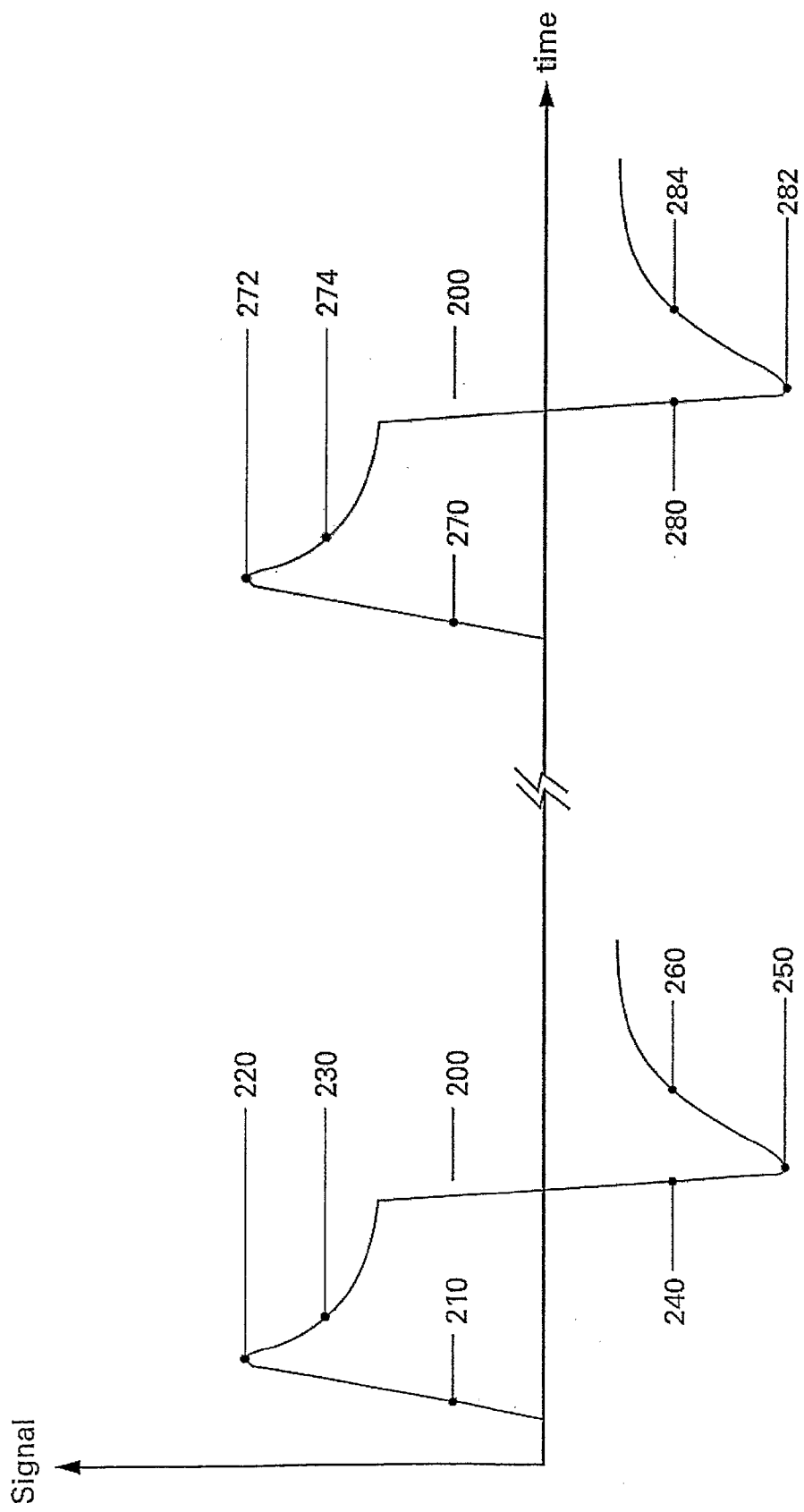
FIG. 2 shows a waveform of an ultrasonic receiver of FIG. 1.

FIG. 2 shows a waveform 200 from an ultrasonic receiver element 121 of FIG. 1, resulting from an embodiment of the method. This shape of the waveform will not be generic, but will depend, on the electrical properties of the instrumentation as well as the sensor itself. The waveform 200 illustrates the sensitivity of the pyroelectric ultrasonic receiver elements 121 to the rate of temperature change. The waveform 200 has a rising portion 210, a peak 220, a decaying portion 230, a falling portion 240 which is generated, immediately after switch off, a negative peak 250, and a negative decaying portion 260 where the sensor returns to thermal equilibrium.

When the ultrasonic transmitter 105 is initially turned on, the temperature of the ultrasonic absorber 123 increases relatively rapidly, causing the ultrasonic receiver element 121 to initially give a large signal. The rise time of the rising portion 210 has been measured, for one embodiment, as 50 ms. After the peak 220, the output of the ultrasonic receiver element 121 gradually decreases as shown by the decaying portion 230. The decaying portion 230 is due to dissipation of thermal energy from the ultrasonic absorber 123 and the ultrasonic receiver element 121, into the surroundings (for example into a coupling fluid such as water). Thus, the rate at which the temperature of the ultrasonic receiver array 120 increases, gradually decreases as the ultrasonic receiver array 120 gradually comes into thermal equilibrium with the surroundings.

The ultrasonic transmitter 105 is then turned off. This causes the temperature of the ultrasonic absorber 123 and ultrasonic receiver element 121 to drop quickly, causing the falling portion 240 and the negative peak 250. The absolute value (that is, the magnitude ignoring the −ve sign) of the negatively decaying portion 260 gradually decreases as the (now cooling) ultrasonic absorber 123 and the ultrasonic receiver element 121 gradually come into thermal equilibrium with the surroundings. The magnitude of the rising portion 210 should be almost identical to the magnitude of the falling portion 240 because the rate at which the ultrasonic absorber 123 and the ultrasonic receiver element 121 warm up is similar to rate to the rate at which they cool down, when the heat source provided by the ultrasonic absorption process is either switch ON or OFF.

Some embodiments of the system 100 are arranged to repeatedly turn the ultrasonic transmitter 105 on and off for an extended time period, which may be required in order for am image to be generated. FIG. 2 also shows a rising portion 270, a peak 272, a decaying portion 274, a falling portion 280, a negative peak 282, and a negative decaying portion 284.

Comparison of one or more of the features 210, 220, 230 with a corresponding one or more of the features 240, 250, 260 can be used to obtain additional information regarding the sample 110. In some arrangements, instead of comparing corresponding features, two or more rising features 210, 270 (or the negative decays 230, 284) may be compared. For example, in order to speed up the acquisition of data, the signal levels generated by the sensor a certain time after switch ON or switch OFF (say 10 ms), be acquired as representative of the time-averaged intensity at the position of a sensor 121 within the array 120.

Figure 3:
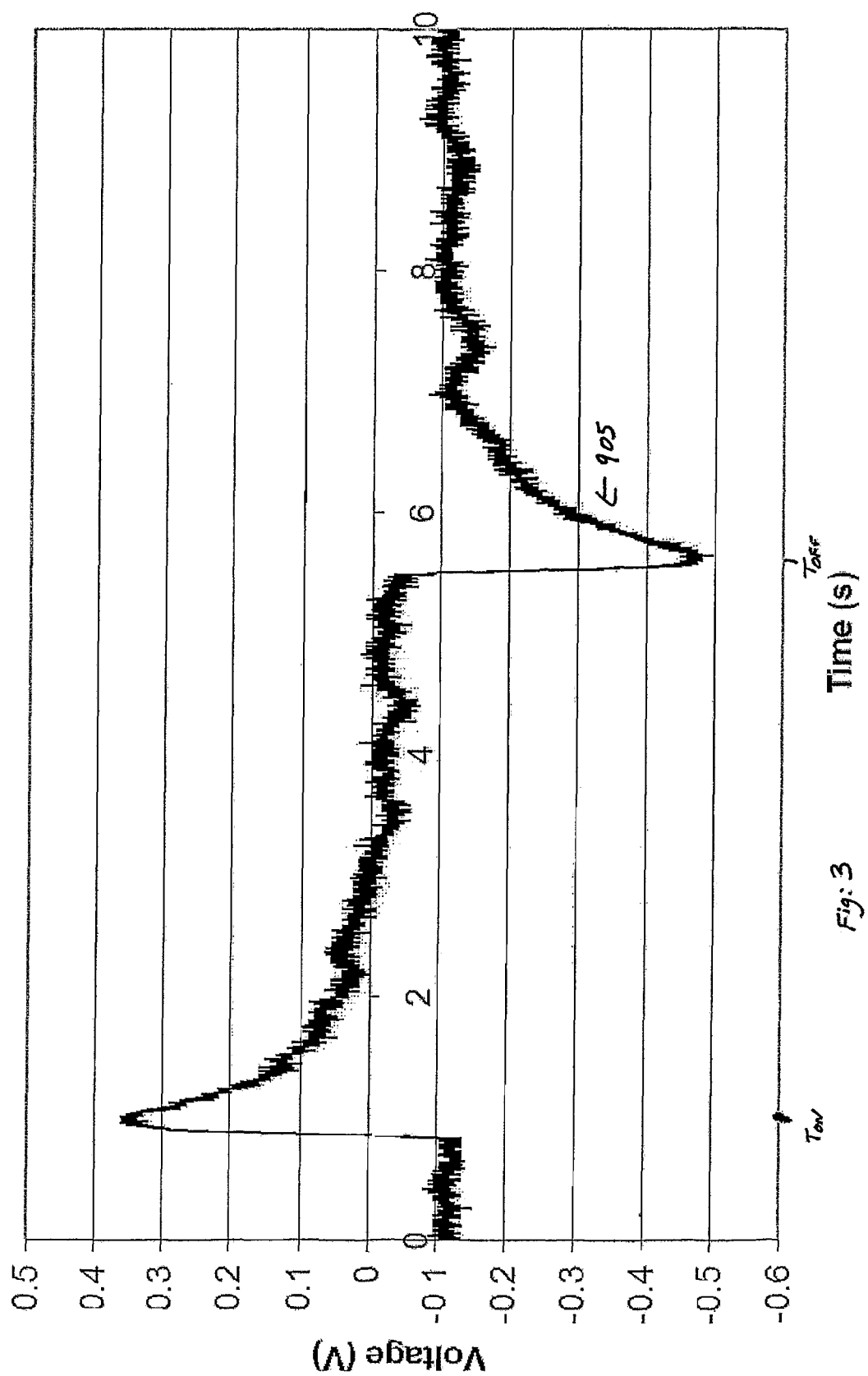
FIG. 3 shows in more detail a waveform corresponding to that of FIG. 2.

The features of this graph are shown in better detail in FIG. 3. From each of the output signals provided by the sensors, key characteristics of the waveform are extracted. There are a number of possibilities but two examples are the switch ON voltage or the switch OFF voltages. It should be noted that for the purposes of this description the switch OFF voltage is defined as the full voltage change from the moment the ultrasound is switch OFF, to the minimum in the voltage—250 and 282 in FIG. 2 and shown better in FIG. 3. In principle, the switch ON and Switch OFF voltages should be substantially equal, but may differ if the tissue is heating up with a consequent change in the acoustic properties of the sample 110.

At time $T_{ON}$, the ultrasound is switched ON, and the pyro voltage increases rapidly. Prior to this, the pyroelectric voltage reading was ambient background noise, that is around 0V (call this $V_0$). The pyro-voltage reaches a maximum about 100 ms after switch ON, the voltage peaking at a particular value, $V_1$. Thereafter, it gradually decreases as thermal equilibrium is approached. The switch ON pyro-voltage is given by $V_1-V_0$.

The rate of temperature increase reduces as thermal conduction mechanisms begin to take effect. At $T_{OFF}$, the ultrasound is switched OFF and the pyro-voltage immediately drops from its value at the point where it switched OFF, of $V_2$.

A short time after switch OFF (again, 100 or so milliseconds later), the pyro-voltage reaches a minimum value ($V_3$), after which it increases and then tends to zero 0 as full thermal equilibrium is reached. The switch OFF pyro-voltage is given by $V_2-V_3$.

The frequencies contained in the waveforms shown in FIG. 3 are typically less than around 10 Hz. Background drifts come from i) background vibrations (some of these will have frequency components which interfere within the pyroelectric signal) and ii) drifts in background temperature which are much slower, that is, frequencies probably below 1 Hz. The example waveform shown in FIG. 3 has frequency components in the frequency range 1 to 3 Hz.

After a while (during which the embodiment of the system 100 is arranged to repeatedly turn the ultrasonic transmitter 105 ON and OFF for an extended time period), the temperature of the intervening sample 110 and (if present) the coupling fluid may have been increased due to their absorption of some of the ultrasonic energy passing along paths 135. Suppose that the regions 115 of the sample represent cancerous regions of tissue.

It is also envisaged that in some embodiments it might be desired to leave the transducer ON for a significant period and allow the tissue in the path to heat up. Cancerous tissue, might have a reduced vascularity and should, in principle, be less able to dissipate heat away; it should heat up more, and its absorption coefficient should consequently increase. There might therefore result in differences in the 'image' generated from Switch ON and Switch OFF voltages, where the transducer is left on for a time period of more than 5 seconds (for example). A 'difference' image (Switch ON-Switch OFF), might then reveal a little more about the nature of the tissue between the transducer and the receiver. An additional possibility is that the 'tissue warming beam' might be a separate transducer which can be applied to a region of the tissue, or maybe the water bath itself is subjected to a change in temperature. When a separate transducer is used, this could be a different type of transducer, not being limited to an ultrasound transducer. Examples include microwave or light transducers.

For a given ultrasonic receiver element 121, a comparison of one or more of the features 210, 220, 230 with a corresponding one or more of the features 270, 272, 274, and/or with a corresponding one or more of the features 280, 282, 284, can indicate a temperature-induced change in the properties of the sample 110. For example, when the sample 110 is tissue, cancerous regions 115 may warm up more than, or less than, non-cancerous regions of the tissue. For cancerous regions 115 in which an ultrasonic property, such as acoustic absorbance, is at least partially temperature dependent, the change in the ultrasonic property can be measured by comparing, for an ultrasonic receiver element 121 that corresponds with path 135a or path 135c, the peak 220 with the peak 272.

Of course, the signal from each ultrasonic receiver element 121 of the ultrasonic receiver array 120 will have its own set of features. In some arrangements of FIG. 1, for a given ultrasonic receiver element 121, features at different times are compared. In other embodiments, features from ultrasonic receiver element 121a at one time are compared with features from (a different) ultrasonic receiver element 121b at a subsequent time. 3-D tomographic imaging of the two warmed (switch OFF) and unwarmed (switch OFF) images may reveal more information about the structure of the sample 110.

Figure 4:
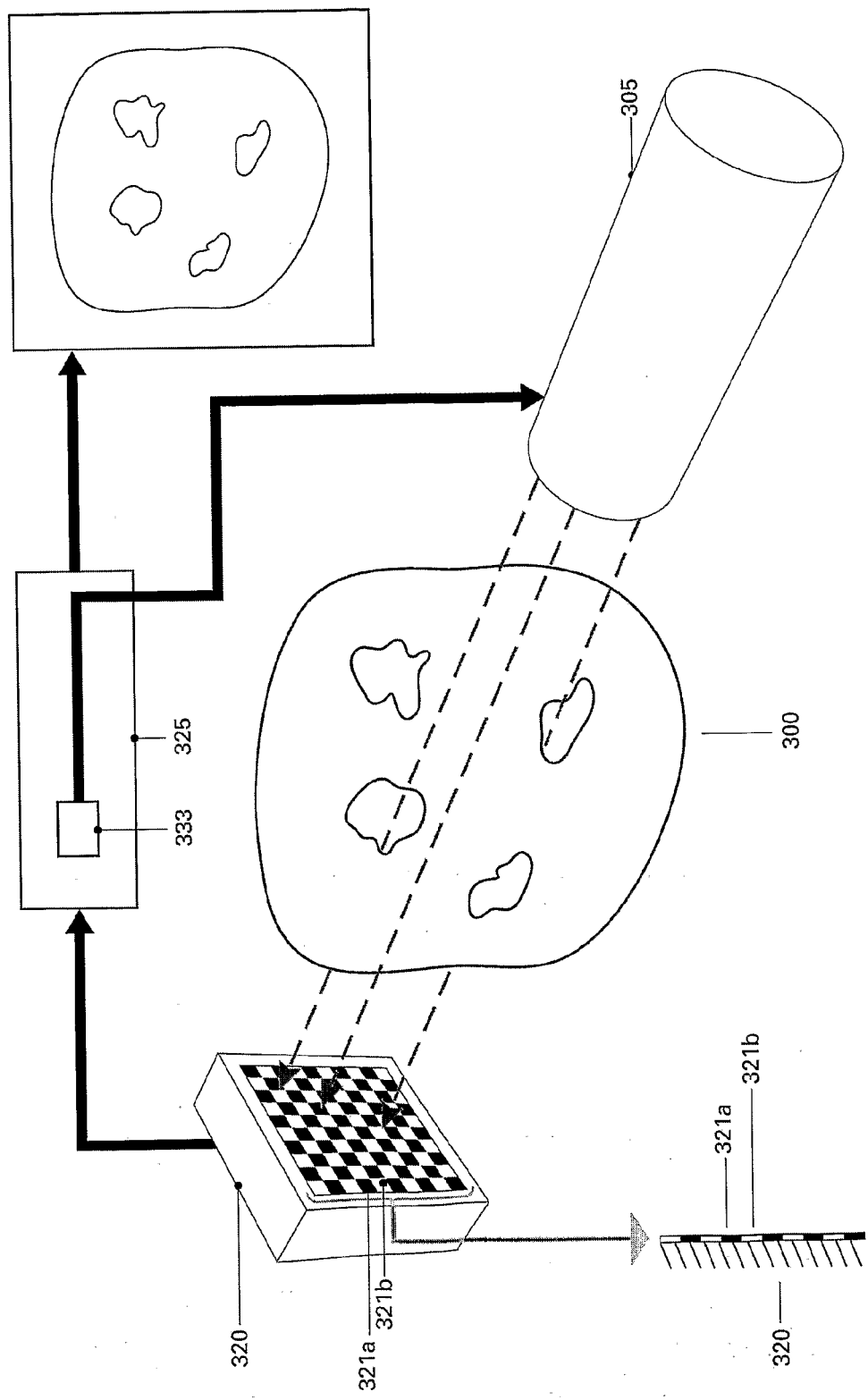
FIG. 4 shows a system that dynamically turns an ultrasonic transmitter on and off in dependence upon the characteristics of a sample being measured.

Referring now to FIG. 4, this shows a system 300 that dynamically turns the ultrasonic transmitter 105 ON and OFF in dependence upon the characteristics of a sample being measured. The system 300 detects peaks 220, 272 and negative peaks 250, 282. The ultrasonic transmitter 105 is turned OFF once a positive peak 220, 272 has been detected, and ON again once a negative peak 250, 282 has been detected.

Pyroelectric sensing devices such as the ultrasonic receiver array 120 are sensitive to changes in temperature and thus the system 300 ensures that as soon as a positive/negative peak has been detected, the transmitter 105 is turned OFF/ON, thus maximising the number of ON/OFF and OFF/ON transitions in a time period.

The system 300 has the benefit that as well as improving the signal-to-noise ratio of measurements (by maximising the number of ON/OFF transitions), the system 300 also may automatically adjust for the propagation delay of the ultrasonic waves through the sample 110. The propagation delay through the water will be of the order of 0.1 ms, so should be much smaller than time taken to see the ON and OFF peaks. Accurately knowing when the transducer is switched ON and OFF, though, will mean that one can more reliably able to measure the peak voltages, as it will be known when to look. It will also make it easier to investigate features such as the signal level a specific time after switch ON and switch OFF.

The signal processing circuitry 325 of the system 300 comprises a peak detector 333 that detects peaks and turns the ultrasonic transmitter 305 ON and OFF. In other embodiments, the peak detector 333 may be replaced by a detector that detects some other feature of the waveform from the ultrasonic receiver array 320, for example the detector may instead detect the rising/falling portions 210, 240 or the decaying portions 230, 260. In other arrangements, the ultrasonic transmitter 305 is not turned OFF but is instead modulated, for example so that the ultrasonic transmitter 305 operates at 100% power and is then reduced to 50% power, and is then increased, for example back to 100% power. It will be appreciated that any change in the operating state of the transistor which can produce a measurable parameter of the type discussed herein could be used.

In one embodiment of the transmitter array, ultrasonic energy can be transmitted at two frequencies or more, for example 1 MHz and 3 MHz. Artefacts associated with the use of ultrasound for 3-D tomographic reconstruction such as reflection and refraction depend only weakly on frequency, so that obtaining images at 1 MHz and 3 MHz, and forming a subtraction image, may be a useful means of reduction the influence of these artefacts on the generated image.

In a further embodiment of FIG. 4 the peak detector 333 is arranged to modulate the ultrasonic transmitter 305 based on the signal from a single element 321 of the ultrasonic receiver array 320. In other arrangements, the peak detector 333 sums, or otherwise combines, the signal from two or more elements 321a, 321b, or from all of the elements 321 of the ultrasonic receiver array 320, to modulate the ultrasonic transmitter 305. Systems in which the signal from a plurality of elements 321 are combined can provide improved reliability in the event of failure of one element 321 of the ultrasonic receiver array 320. Such systems can also allow for the fact that the ultrasonic energy from the ultrasonic transmitter 305 might be received by some elements 321 of the ultrasonic receiver array 320 before other elements 321 of the array 320; for example, FIG. 4 shows that a wave front from the ultrasonic transmitter 305 will travel a slightly further distance to elements 321 at the corners of the array 320 compared to the distance to elements 321 at the centre of the array 320.

Figure 5:
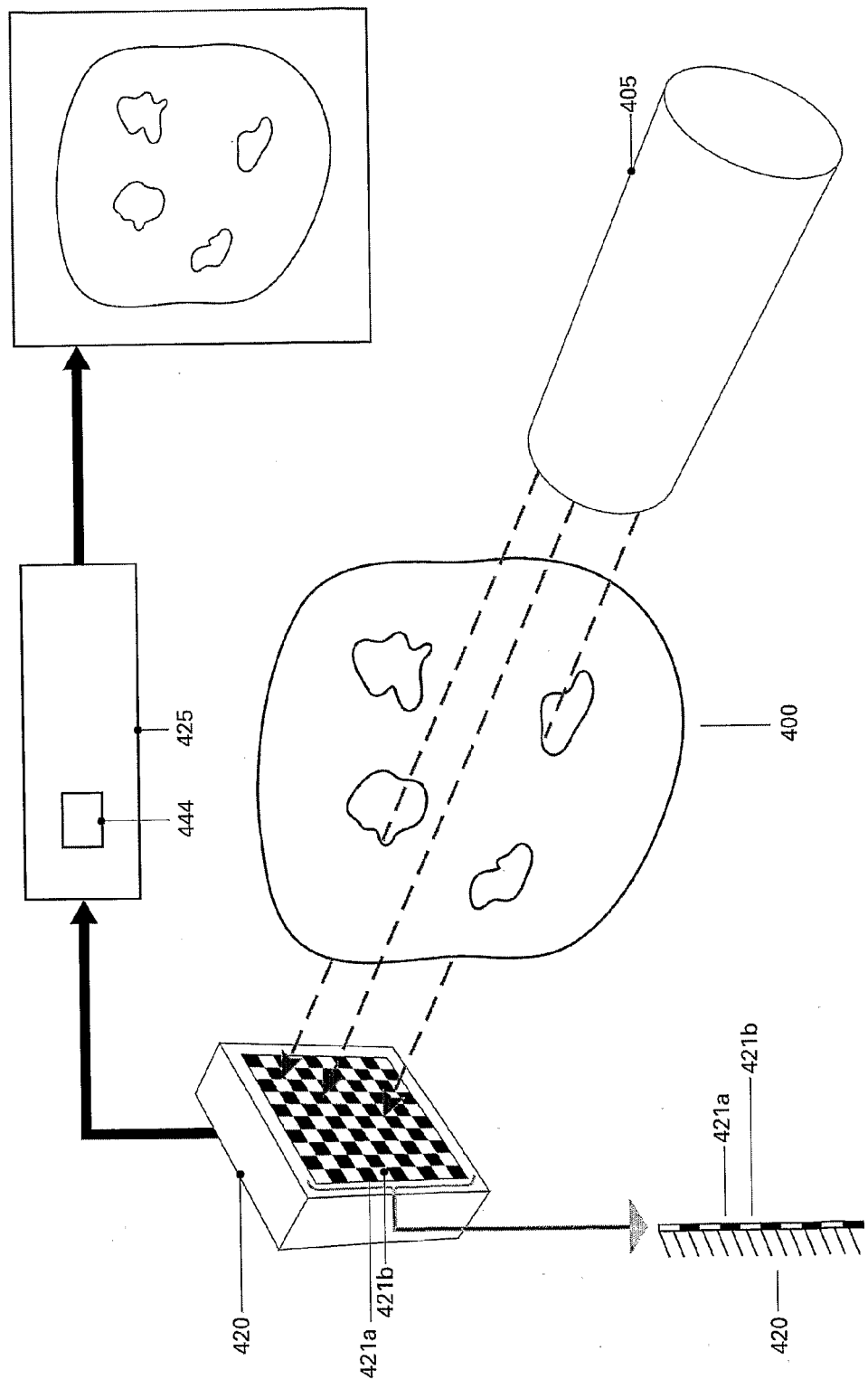
FIG. 5 shows a system that calibrates an ultrasonic receiver to null out unwanted accelerometer sensitivity of the ultrasonic receiver.

Referring now to FIG. 5, this shows a system 400 designed to calibrate the ultrasonic receiver array 420 to null out unwanted accelerometer sensitivity or short-term drifts in the temperature of the ultrasonic receiver array 420. Pyroelectric materials tend also to be piezoelectric and thus the ultrasonic receiver array 420 may have some sensitivity as an accelerometer; the system 400 distinguishes the (unwanted) accelerometer signals from the (wanted) ultrasound signals. The system 400 may be beneficial when there is background noise, for example resulting from structurally borne vibration. As in many practical applications there is likely to be background noise, the whole scanning system/gantry could be located on anti-vibration mounts or provided with other vibration compensation mechanisms to reduce or minimize the effects of the background noise.

The signal processing circuitry 425 of the system 400 comprises background removal circuitry 444 that can be used to compensate for an unwanted accelerometer background signal. The system 400 operates first in a background compensation mode, in which the ultrasonic transmitter 405 is turned OFF and in which the signal from the ultrasonic receiver array 420 is measured over a period of time, and uses this information to extrapolate the dependence at later times, more particularly at the instant the peak in the signal level (220) is attained. The system 400 then turns the ultrasonic transmitter 405 ON, and subtracts the extrapolated background (OFF) signal from the (ON) signal from the ultrasonic receiver array 420, thus compensating for accelerometer sensitivity. This approach may also be used for the switch OFF measurement and works best for slowly varying background signals, for example, temperature drift.

In some embodiments, the frequency components contained in the accelerometer background signals will interfere with those of the desired pyroelectric signal. In one embodiment the system provides for measuring the background output signal of one or more individual sensors at (or as close as possible) at the same time as the pyroelectric signal is measured on the vast majority of sensors. This can be done by shielding the background sensors from the effects of heating of their backing in ways described below. This background signature might be taken from a single sensor whose vibration is representative of the whole receiver array or may be an average of the signal from a few sensors distributed throughout the array. The compensated signal can then simply be the difference between the time dependent voltage of the pyroelectrically active 'live' array and the time dependent background signal. Key features of the waveform shown in FIG. 3, are then extracted from this vibration compensated array.

Figure 6:
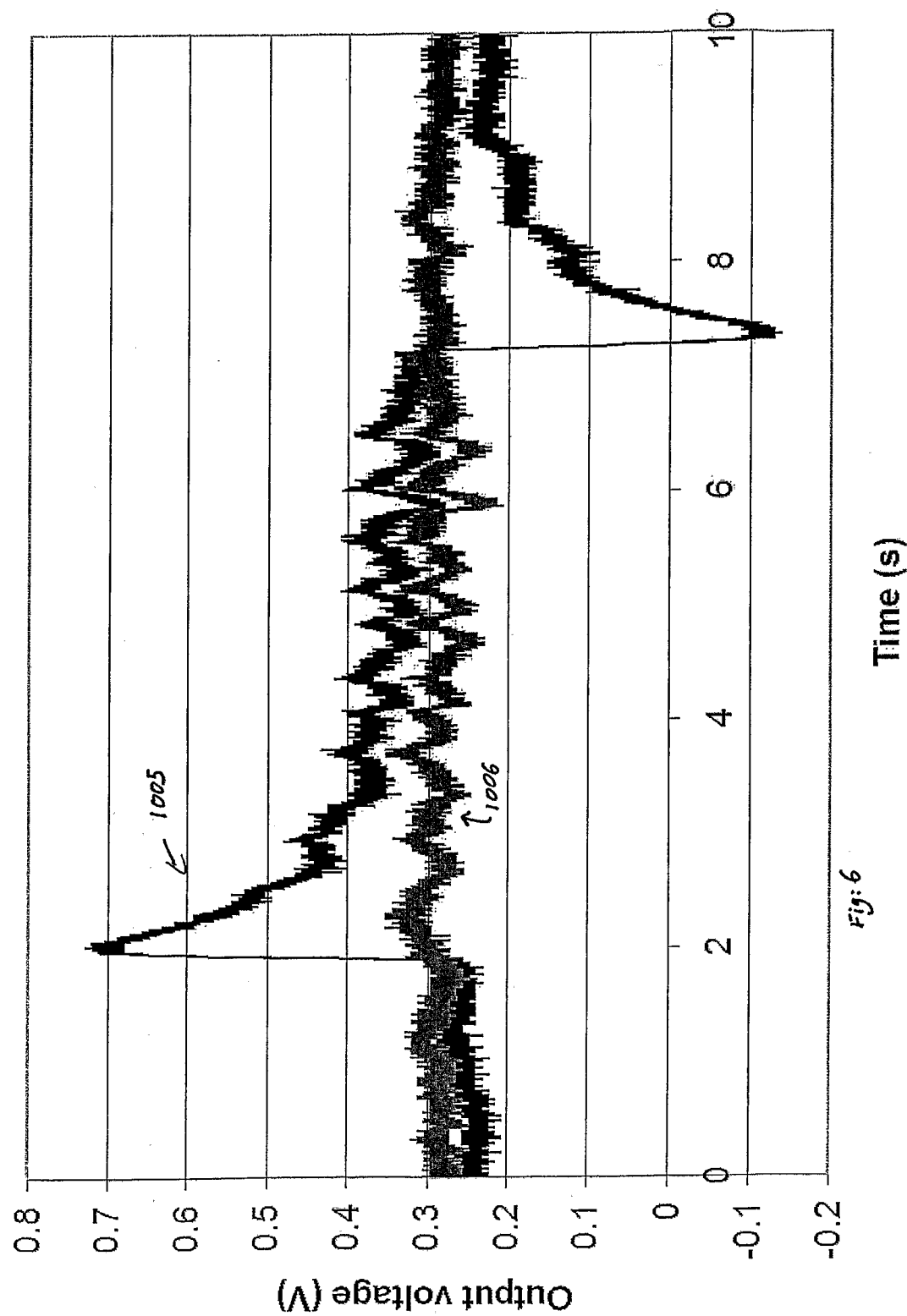
FIG. 6 shows in more detail a waveform associated with the system of FIG. 5.

FIG. 6 below shows how this might work using a dual electrode arrangement where ultrasound is only applied to one. The reference electrode, shielded from the ultrasound power, picks up the background vibration signal. In terms of a low-Pass filter, the upper cut-off may be 20 Hz or so to minimise any mains electrical pick-up. FIG. 6 shows the output from two sensor electrodes; the test electrode to which the acoustic signal has been applied and the reference electrode which has been shielded from the acoustic signal.

More particularly, FIG. 6 shows a signal 1005 measured from an ultrasonic receiver that includes both a thermal effect and an (unwanted) accelerometer effect. A signal 1006 includes only the accelerometer effect and this may be subtracted from the signal 1005 in order to reduce sensitivity to accelerometer effects.

In some arrangements of FIG. 5, the background removal circuitry 444 analyses the background noise. For example, if there is a noise signal at 100 Hz (for example mechanical vibration from a 50 Hz mains powered transformer) then the background removal circuitry 444 determines the 100 Hz noise signal and removes the 100 Hz noise. In some embodiments of FIG. 4, the background removal circuitry 444 uses a notch filter to remove the 100 Hz noise signal; such embodiments have the disadvantage that any wanted ultrasound signals in the 100 Hz range will also be removed. Therefore, in other arrangements the background removal circuitry 444 synthesises a 100 Hz signal and subtracts the synthesised 100 Hz signal from the ultrasound signal in order to null out the 100 Hz noise signal.

The background removal circuitry 444 may also periodically re-calibrate itself, for example every second, to ensure that the 100 Hz synthesised signal is phase locked to the background accelerometer signal.

In other embodiments, the background removal circuitry 444 may re-calibrate more frequently. For example, where the systems 300 and 400 are combined, the peak detector 333 may be arranged, after each peak, instead of immediately turning the ultrasonic transmitter 305/405 ON or OFF, to wait until the decaying portions 230, 260 and then sample the background accelerometer noise signal.

The background removal circuitry 444 can also reduce the sensitivity of the system 400 to non-accelerometer background noise, for example uncorrelated extraneous electrical signals that are electrically coupled to the ultrasonic receiver array 420.

In arrangements of FIG. 5 where the system 400 comprises an ultrasonic receiver array 420 (as opposed to just a single ultrasonic receiver element 421*a*), the background removal circuitry 444 may compensate for background noise based on a single element 421*a*, or the noise of two elements 421*a*, 421*b* may separately be compensated, or the array 420 may be divided into two or more regions that are separately compensated.

Figure 7:
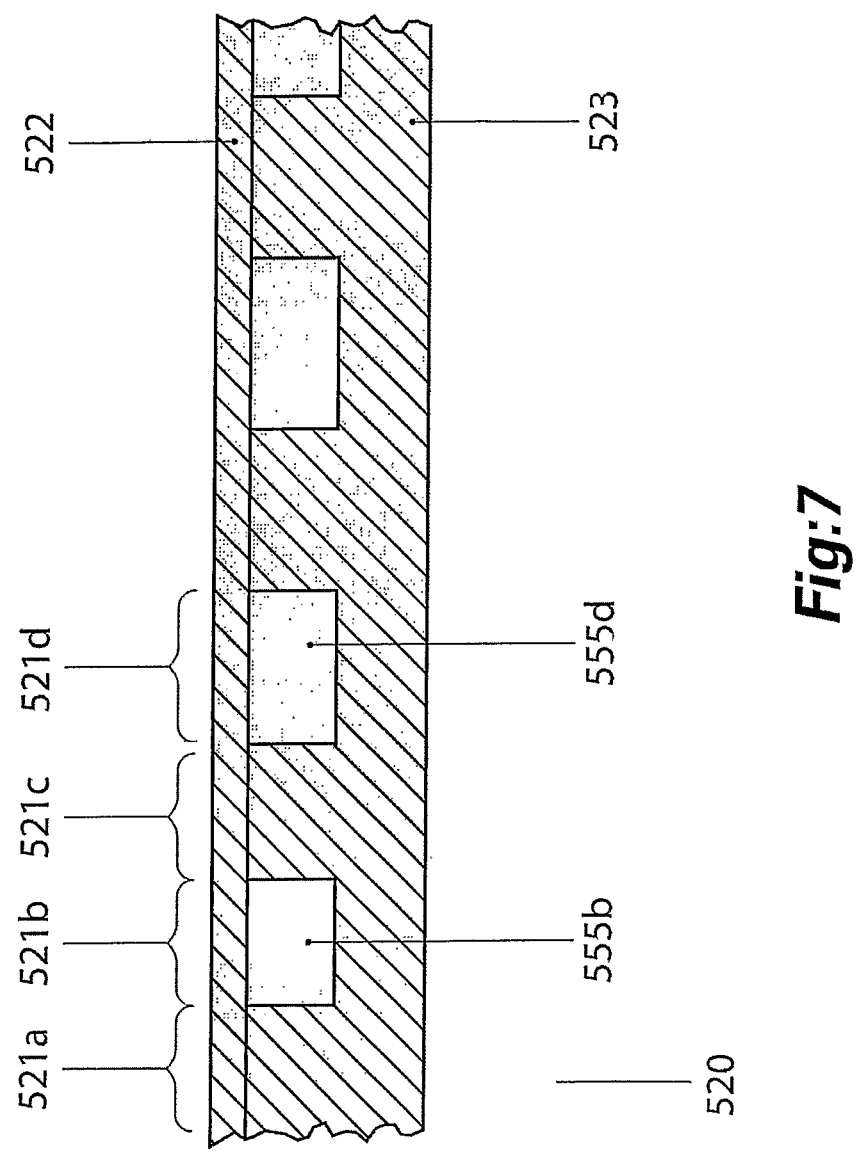
FIG. 7 shows a cross-sectional view of an ultrasonic receiver that has cavities to facilitate nulling out of unwanted accelerometer sensitivity.

Referring now to FIG. 7, this shows a cross-sectional view of an ultrasonic receiver 520 that has cavities 555 to facilitate nulling out of unwanted accelerometer sensitivity. The ultrasonic receiver 520 comprises a PVDF film 522 which is divided into separate elements 521*a*, 521*b* etc. Some of the elements, for example elements 521*a* and 521*c*, overlie ultrasonic absorbing polyurethane layer 523. This layer is preferably formed of polyurethane rubber with small inclusions of air, for example 10-20 μm diameter bubbles to boost ultrasonic absorption. This layer will hereinafter be described as a foam layer and encompass alternatives to such a polyurethane rubber.

Other elements, for example elements 521*b* and 521*d*, overlie respective empty cavities 555*b*, 555*d*.

In FIG. 5 the cavities 555 are, in effect, surface depressions in the foam layer 523. In other arrangements, the depressions may extend all the way through the foam layer 523.

The elements 521*a* and 521*c* are backed by the foam layer 523 and thus these elements will produce an electrical signal, due to the pyroelectric effect, in response to a temperature change (e.g. a rise) caused by incoming ultrasonic energy. The elements 521*b* and 521*d* are not backed by the foam layer 523 and are thus substantially insensitive to heating caused by the incoming ultrasonic energy.

However, the elements 521*b* and 521*d* have an accelerometer response that is substantially identical to the accelerometer response of elements 521*a* and 521*d*. The signal processing circuitry 125 can therefore compensate for the accelerometer response by subtracting the signal from element 521*b* from the signal from element 521*a*, and by subtracting the signal from element 521*d* from the signal from element 521*c*.

In other embodiments of FIG. 7, instead of each ultrasonic sensing element 521*a*, 521*c* having its own respective compensating element 521*b*, 521*d*, the ultrasonic receiver 520 is provided with a single compensating element that is shared between the ultrasonic sensing elements 521*a*, 521*c*. Alternatively, the ultrasonic receiver 520 may have a plurality of such elements, for example, four compensating elements, each of which is shared by a plurality of ultrasonic sensing elements. It is preferred not to have many 'dead' elements in the array as this might affect the imaging, and the preferred implementation would include a handful around the edges of the overall array.

In other arrangements of FIG. 7, instead of overlying a cavity 555 or a through passage, the elements 521*b* and 521*d* overlay a material that has a high heat capacity compared to the foam layer 523. For example, the elements 521*b* and 521*d* may overly a copper substrate (instead of the foam layer 523). When incoming ultrasonic energy is received by the ultrasonic receiver 520, the temperature of the elements 521*b*, 521*d* does not change appreciably when compared to the temperature by which the elements 521*a*, 521*c* change.

In some implementations, the material does not need to have a high capacity but is thermally connected by a good thermal conductor, for example a heat pipe, to a refrigerator so that the material has an high effective heat capacity.

It is envisaged in some embodiments that rather than have the cavities in FIG. 7 filled with air, the cavities would be filled with a low absorption polymer material so that heating in the immediate vicinity of the sensor is minimised. The skilled person will appreciate the practical possibilities for this variation.

In yet other arrangements of FIG. 7, the elements 521*a*, 521*c* overlay a first ultrasonic absorber, and the elements 521*b*, 521*d* overlay a second ultrasonic absorber. The first and second ultrasonic absorbers have different thermal and acoustic properties (for example, heat capacity and/or thermal conduction, or absorption). The first and second ultrasonic absorbers may be arranged in an alternating arrangement similar to a chess board. All of the elements 521 may have a substantially similar accelerometer sensitivity but the elements 521*a*, 521*c* have a first sensitivity to incoming ultrasonic radiation whereas the elements 521*b*, 521*d* have a second sensitivity to incoming ultrasonic radiation. Thus the accelerometer sensitivity of elements 521*a*, 521*c* can be removed by subtraction of the signal from elements 521*b*, 521*d*. The accelerometer sensitivity of elements 521*b*, 521*d* can be removed by subtraction of the signal from elements 521*a*, 521*c*. The resulting signals from the elements 521 (that is, after subtraction) may require processing to take account of the different thermal properties of the first and second ultrasonic absorbers, and thus of the different sensitivities to incoming ultrasonic energy of the elements 521a, 521c and 521b, 521d. Alternatively, the first and second ultrasonic absorbers may have identical thermal properties but different ultrasonic properties. More generally, the first and second ultrasonic absorbers may have different thermal and/or ultrasonic properties (for example, the first ultrasonic absorber may absorb most of the ultrasonic radiation within a distance of 0.2 mm whereas the second ultrasonic absorber may absorb most of the ultrasonic radiation within a distance of 2 mm). Such arrangements may be combined with arrangements of FIG. 7 discussed above.

Figure 8:
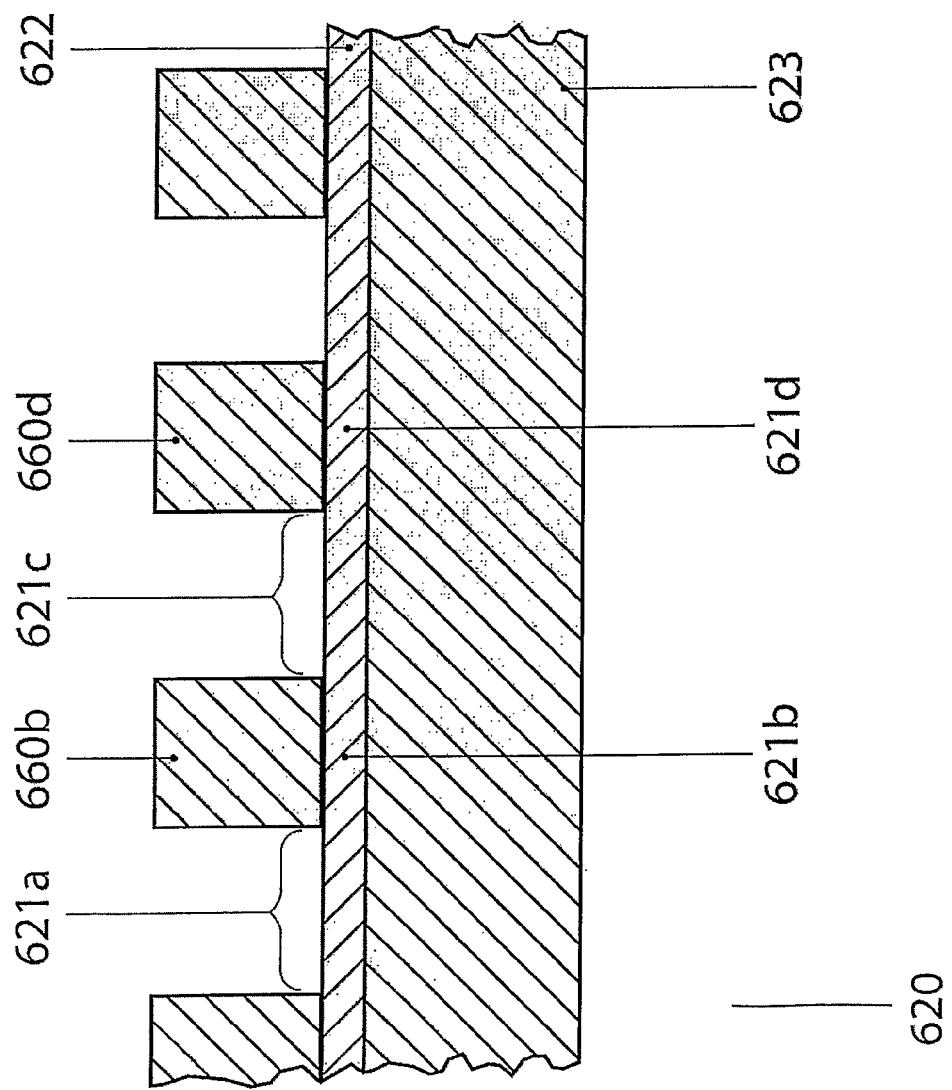
FIG. 8 shows a cross-sectional view of an ultrasonic receiver that has absorbing regions to facilitate nulling out of unwanted accelerometer sensitivity.

Referring now to FIG. 8, this shows a cross-sectional view of an ultrasonic receiver 620 that has absorbing regions 660 to facilitate nulling out of unwanted accelerometer sensitivity. Even though in this embodiment these regions are absorbing, they could instead be reflecting in terms of reflecting the ultrasound away from the backing layer.

The ultrasonic receiver 620 comprises a PVDF film 622 which is divided into separate elements 621a, 621b etc. The elements 621 overlay an ultrasonic absorbing polyurethane foam layer 623. Some of the elements, for example elements 621b and 621d, are overlaid by respective absorbing regions 660b, 660d. In FIG. 6, all of the elements 621 overly a respective portion of the polyurethane foam layer 623. Only the elements 621b, 621d are overlaid by absorbing regions 660b, 660d.

Compared to the elements 621a, 621c, the elements 621b, 621d are relatively insensitive to incoming ultrasonic energy; this is because incoming ultrasonic energy will be absorbed by the absorbing regions 660b, 660d before the ultrasonic energy can heat up the elements 621b, 621d. The outermost portions of the absorbing regions 660b, 660d will become heated by incoming ultrasonic energy. However, provided that the thickness of the absorbing regions 660 is sufficient (e.g. 5 mm), the heat will not be appreciably conducted from the front of the absorbing regions 660 to the rear of the absorbing regions 660 (it is the rear of the elements 621b, 621d that is in thermal communication with the elements 621b, 621d). In some embodiments, the very top layer of these 'islands' could be covered by a metal which dissipates any heat away quickly. The thickness of this metal might also be optimised to maximise the reflectivity of the elements 660.

All of the elements 621 may have a substantially similar accelerometer sensitivity. The signal from the elements 621b, 621d can be removed, for example by subtraction, from the signal from the elements 621a, 621b to compensate for unwanted accelerometer sensitivity. In some arrangements of FIG. 6, the accelerometer sensitivity of the elements 621b, 621d may be a higher, for example three times more sensitive, than the accelerometer sensitivity of the elements 621a, 621c (the scale factor of three being due to the extra mass, due to the absorbing regions 660b, 660d, on the elements 621b, 621d). In such arrangements the signal from the elements 621b, 621d may be reduced by a factor of three before being subtracted from the signals of the elements 621a, 621c.

In FIG. 8 the absorbing regions 660 comprise ultrasonic absorbing polyurethane foam although other materials or structures may be used instead. For example, a material that reflects ultrasonic energy may be used instead of polyurethane foam to isolate the regions 621b, 621d from incoming ultrasonic energy.

The structures and arrangements described above for FIGS. 7 and 8 may be combined. The resulting combination may have one or more cavities 555 and one or more absorbing regions 660. In some combinations, an absorbing region 660 may overly a cavity 555 (with an intervening element 521, 621).

Figure 9:
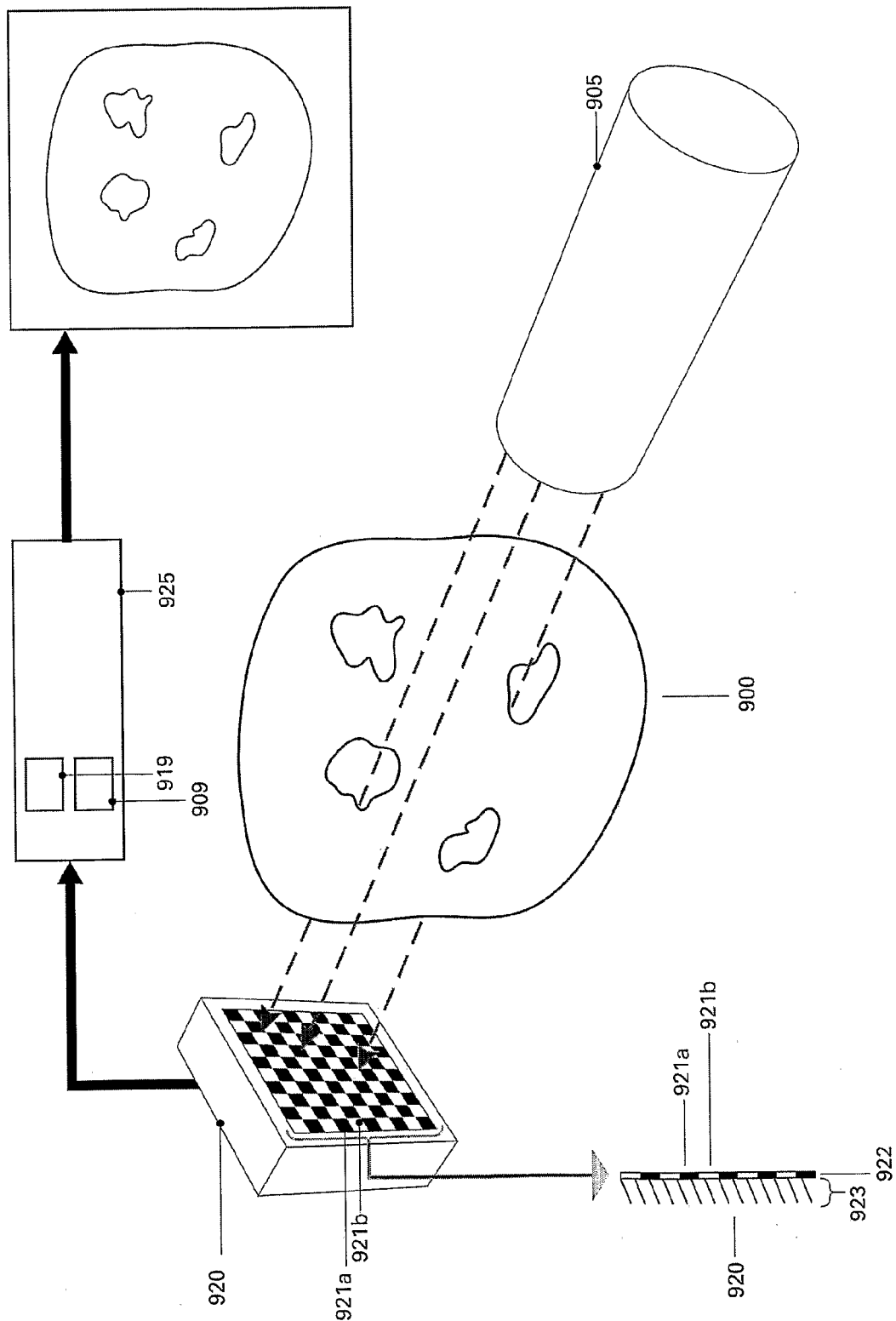
FIG. 9 shows a system that uses an ultrasonic receiver to make both phase-sensitive and phase insensitive measurements.

Referring now to FIG. 9, this shows a system 900 which uses an ultrasonic receiver to make both phase-sensitive and phase-insensitive measurements. The system 900 is similar to the system 100 of FIG. 1 but includes signal processing circuitry 925 that includes a low frequency path 909 and a high frequency path 919.

The low frequency path 909 operates in a similar manner to the signal processing circuitry 925. That is, the low frequency path 909 detects the signal from a PVDF temperature sensitive layer 922 based on temperatures changes sensed by the temperature sensitive layer 922 in response to ultrasonic absorption by the ultrasonic absorber 923. The low frequency path 909 may have a bandwidth in the Hz-to-kHz range. The low frequency path 909 may include a low pass or band pass filter; a band pass filter is generally preferred to avoid amplification of DC offsets.

The high frequency path 919 detects the signal from the PVDF temperature sensitive layer 922 based on the piezoelectric response of the polymer. It will be recalled that pyroelectric substances tend to be both piezoelectric and pyroelectric. Incoming ultrasonic radiation will cause an acoustic pressure wave that will be coupled into the PVDF, causing a deformation of the thickness of the membrane and a piezoelectric response leading to a signal in the MHz range (or at whatever frequency is used for the ultrasonic energy, typically upwards of 20 kHz and below 10 MHz). Thus, whereas the low frequency path 909 measures the time-averaged heating effect of the ultrasonic waveform, the high frequency path 919 measures the actual pressure waveform transmitted through the sample, allowing conventional through transmission imaging techniques to be employed. The high frequency path 919 may include a high pass filter or a band pass filter; a band pass filter is generally preferred to limit the noise bandwidth of the high frequency path 919 and thus to improve the signal-to-noise ratio.

In some embodiments, the system 900 has an ultrasonic receiver 920 that has a single ultrasonic receiver element 921. Other embodiments of the system 900 have an ultrasonic receiver 920 that has a plurality, for example an array, of ultrasonic receiver elements 921.

The system 900 can be used to measure to image the properties of a sample 910 in three ways:—

(i) (phase insensitively) by recording how much acoustic energy is absorbed by the sample (by determining how much of the ultrasonic intensity from the ultrasonic transmitter 905 is absorbed by the sample 910 before reaching the ultrasonic receiver 920);

(ii) (phase sensitively) by measuring the acoustic pressure amplitude transmitted through the sample and how this varies spatially;

(iii) by using the high frequency signals to image the speed of sound i.e. by recording the arrival time of the ultrasonic wave and how this varies with spatial position.

With regard to (i), some arrangements of the system 900 (for example those having a single ultrasonic receiver element 921) determine the energy absorption by measuring the level of the signal received at the ultrasonic receiver 920. Other arrangements (for example those having a plurality of ultrasonic receiver elements 921) compare the levels of the signals received by two or more ultrasonic receiver elements 921 of the ultrasonic receiver 920.

With regard to (ii), some arrangements of the system 900 (for example those having a single ultrasonic receiver element 921) determine the phase by comparing the received phase with the transmitted phase. Other arrangements (for example those having a plurality of ultrasonic receiver elements 921) compare the phases of the signals received by two or more ultrasonic receiver elements 921 of the ultrasonic receiver 920. These phases are used to derive the speed of sound as given in iii).

It is envisaged that some implementations could be provided with dual applications, that is piezo and pyro, in order to be able to compare the two from the two methods. It is believed that this will provide important additional information about the inhomogeneity of the intervening medium, which can be useful in terms of assessing whether the are significant inclusions which will lead, for example, to differences in imaging using the techniques ii) and iii), given above.

In other embodiments, instead of the ultrasonic receiver 920 comprising PVDF elements 921, the array may instead comprise one or more temperature sensors (such as thermocouples) together with one or more hydrophones. Preferably, the number of thermocouples is the same as the number of hydrophones.

Figure 10:
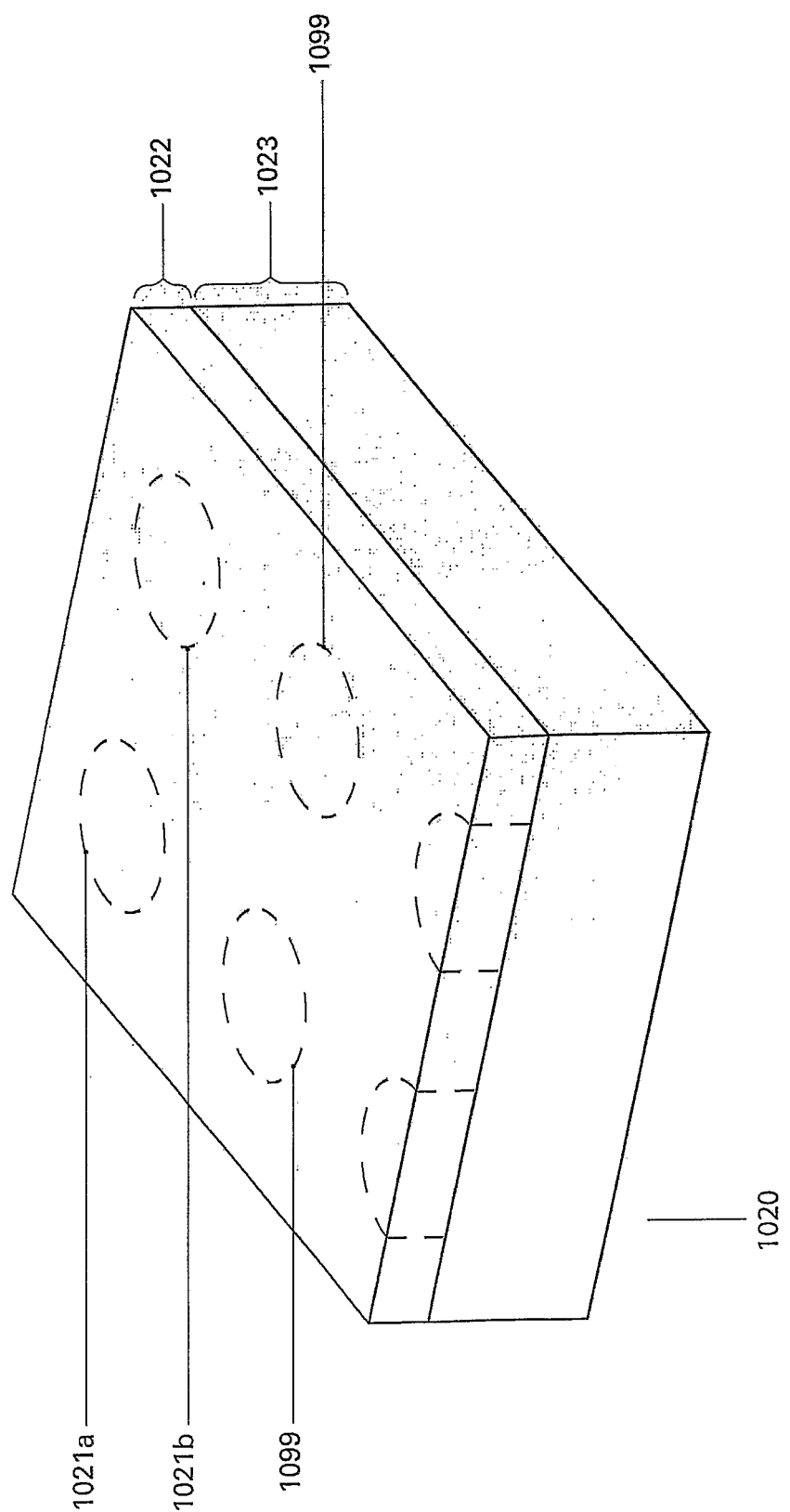
FIG. 10 shows a perspective cross-sectional view of an ultrasonic receiver array that comprises discrete poled regions.

Referring now to FIG. 10, this shows a perspective cross-sectional view of an ultrasonic receiver array 1020 that comprises discrete poled regions 1099 of a PVDF layer 1022. Those skilled in the art will appreciate that pyroelectric and/or piezoelectric materials are often poled to induce a permanent remnant polarization. Typically, a material is poled by heating it up to just below the Curie temperature while applying a strong DC electric field, and then allowing the material to cool while the DC electrical field is maintained. When the material has cooled, the DC electrical field may be removed and the poled material will exhibit a remnant polarization.

Each ultrasonic receiver element 1021 comprises a respective poled region 1099 that overlies an ultrasonic absorber 1023. An advantage of having discrete poled regions 1099 is that the poled regions 1099 are separated by a non-poled region of PVDF 1098. The non-poled region of PVDF 1098 provides the advantage that cross-talk between, for example, adjacent ultrasonic receiver elements 1021a, 1021b is reduced.

The ultrasonic receiver array of FIG. 10 may be combined with the ultrasonic receiver array of FIG. 5, 6 or 7. The ultrasonic receiver array of FIG. 10 may be used, without the ultrasonic absorber 1023, as a hydrophone array.

Figure 11:
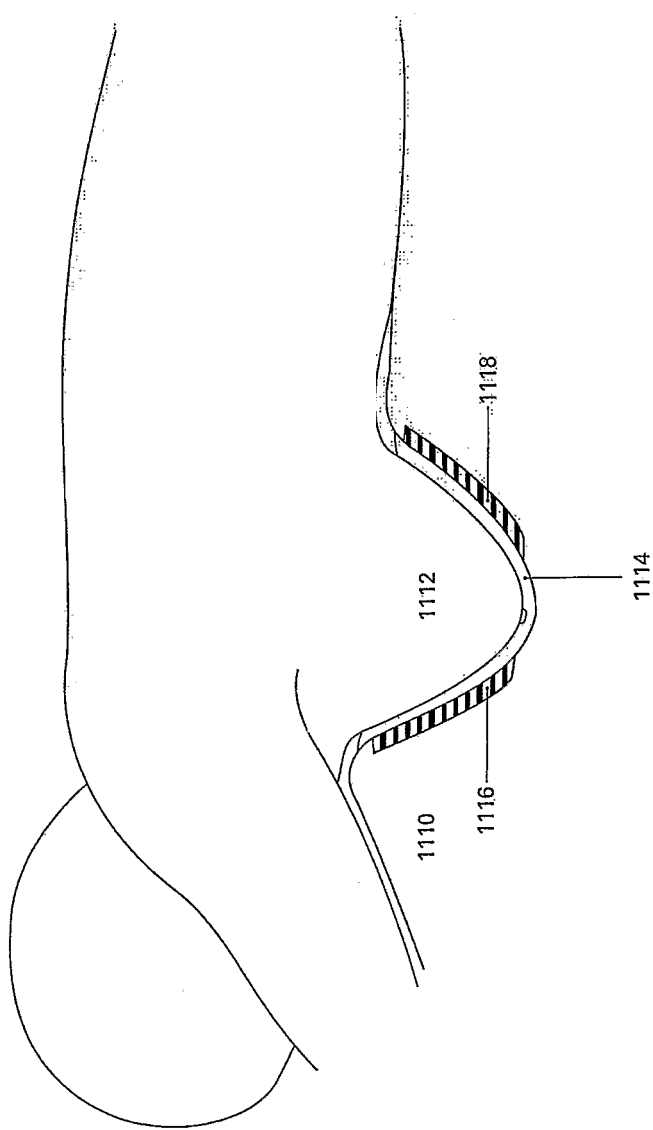
FIG. 11 is a sketch of an embodiment of mammography apparatus.

Referring now to FIG. 11, there is shown an embodiment of mammography apparatus embodying the teachings herein. The apparatus includes a couch 1110 upon which the patient can lie face downwards with their breast(s) 1112 positioned within a central water-filled reservoir 1114. Around the walls of the reservoir 1114 there are positioned the ultrasonic receiver and transmitter elements 1116, 1118. These elements are preferably in the form of arrays, although the transmitter might be a single large transmitter. Although in FIG. 11 the elements 1116 and 1118 are shown to be substantially planar, it is envisaged that they might be curved to follow the curvature of the walls of the chamber 1114. The sensors 1118 are able to "scan" around the breast to acquire the data required for 3-D tomographic reconstruction.

A transfer fluid such as water may be used to improve the coupling of ultrasonic energy from the ultrasonic transmitter 1116 to the sample 1112, and/or to improve the coupling from the sample 1112 to the ultrasonic receiver array 1118. The properties of the water couplant medium may be modified to improve the images generated, for example through the addition of cavitation inhibitors or solutes which match the speed of sound to that of breast tissue.

Those skilled in the art will appreciate that the various Figures, arrangements and embodiments described above can be combined and/or amended. In some aspects, the disclosures above can be regarded as equivalent to methods. For example, the system 100 of FIG. 1 provides a method of ultrasound imaging by measuring the attenuation of different regions 115 of a sample 110.

The disclosures in British patent application number 0901022.4, from which this patent application claims priority, and in the abstract accompanying this application are incorporated herein by reference.

The invention claimed is:

1. Imaging apparatus for imaging the spatial distribution of the acoustic properties of a sample, the apparatus comprising:
   at least one ultrasonic transmitter operable to generate an ultrasonic beam across an imaging area;
   at least one ultrasonic receiver sensitive to intensity of an ultrasonic field generated by the transmitter or transmitters, the at least one ultrasonic receiver comprising:
   an ultrasonic absorber; and
   a film which is divided into a plurality of separate elements comprising:
      at least one pyroelectric ultrasonic sensing element in thermal communication with the ultrasonic absorber, which is sensitive to heating caused by the ultrasonic field and which has an accelerometer response; and
      at least one pyroelectric compensation element which is substantially insensitive to heating caused by the ultrasonic field and which has an accelerometer response substantially similar to that of the at least one pyroelectric ultrasonic sensing element;
   wherein the at least one ultrasonic receiver is arranged to sense the ultrasonic field in a part of the imaging area; and
   signal processing circuitry operable to process a signal from the at least one ultrasonic receiver to derive therefrom an intensity measure across said imaging area, and thus to derive a spatial distribution of the acoustic properties of a sample in the field across said imaging area, wherein the signal processing circuitry is further operable to remove the signal from the at least one pyroelectric compensation element from the signal from the at least one pyroelectric ultrasonic sensing element so as to compensate for the accelerometer response of the at least one pyroelectric ultrasonic sensing element.

2. Imaging apparatus according to claim 1, wherein the at least one receiver provides an intensity measurement of the ultrasonic field averaged over time.

3. Imaging apparatus according to claim 1, wherein the at least one ultrasonic receiver comprises a pyroelectric material.

4. Imaging apparatus according to claim 1, wherein the at least one ultrasonic receiver comprises a pyroelectric layer and a backing layer absorbent to ultrasound.

5. Imaging apparatus according to claim 1, wherein the at least one ultrasonic receiver has a receiver area smaller than the imaging area.

6. Imaging apparatus according to claim 5, wherein the at least one receiver is a point-type receiver.

7. Imaging apparatus according to claim 5, wherein the at least one receiver has a diameter of 2 millimeters or less.

8. Imaging apparatus according to claim 5, wherein the at least one receiver has a diameter of 0.5 millimeters or less.

9. Imaging apparatus according to claim 1, wherein the at least one transmitter is operable to generate an ultrasonic beam smaller than the imaging area.

10. Imaging apparatus according to claim 9, wherein the transmitter or transmitters are movable across the imaging area and/or there is provided an array of transmitters covering the imaging area.

11. Imaging apparatus according to claim 1, wherein at least one of the ultrasonic transmitter and receiver comprises an array of elements.

12. Imaging apparatus according to claim 11, wherein said array is a two-dimensional array.

13. Imaging apparatus according to claim 11, wherein the signal processing circuitry is operable to compare, for said elements, a feature from a first time with a feature from a second time.

14. Imaging apparatus according to claim 13, wherein signal processing circuitry is operable to compare a feature from a first element of said array at a first time with a feature from a second element or said array at a second time.

15. Imaging apparatus according to claim 1, including a positioner for positioning a sample in a path between the ultrasonic transmitter or transmitters and the receiver or receivers.

16. Imaging apparatus according to claim 1, wherein the apparatus is a mammography machine.

17. Imaging apparatus according to claim 1, wherein the signal processing circuitry comprises a low pass filter to accept signals having a frequency corresponding to a thermal change of the ultrasonic receiver but to reject higher frequency signals.

18. Imaging apparatus according to claim 1, wherein the signal processing circuitry is operable to measure one or more first features at a first time and to measure one or more second features at a second, subsequent, time.

19. Imaging apparatus according to claim 18, wherein the signal processing circuitry is operable to compare the one or more first features with the one or more second features to obtain information regarding the sample.

20. Imaging apparatus according to claim 18, wherein the one or more features comprise one or more of: a rising portion, a peak, a decaying portion, a falling portion, a negative peak, and a negative decaying portion.

21. Imaging apparatus according to claim 1, wherein the signal processing circuitry comprises a detector operable to detect features in the signal and modulate the ultrasonic transmitter in response to the features.

22. Imaging apparatus according to claim 21, wherein the detector is operable to detect peaks.

23. Imaging apparatus according to claim 21, wherein the detector is operable to turn the ultrasonic transmitter on and off.

24. Imaging apparatus according to claim 21, wherein the ultrasonic receiver comprises an array of elements, and wherein the detector is operable to combine or compare the signals from two or more elements and modulate the ultrasonic transmitter on the basis of the combined signal.

25. Imaging apparatus according to claim 1, wherein the signal processing circuitry comprises background removal circuitry operable to reduce the sensitivity of the system to a background signal detected by the ultrasonic receiver.

26. Imaging apparatus according to claim 25, wherein the background removal circuitry is operable to filter the background signal from the ultrasonic receiver using a notch filter and/or to synthesize a representation of background noise, and to subtract the synthesized-representation from the signal from the ultrasonic receiver.

27. Imaging apparatus according to claim 25, wherein the ultrasonic receiver comprises an array of elements, and wherein the background removal circuitry is operable to perform a first background removal for some of the elements, and to perform a second, different, background removal for other elements.

28. Imaging apparatus according to claim 1, wherein the at least one ultrasonic receiver comprises a pyroelectric element overlying an ultrasound absorber.

29. Imaging apparatus according to claim 28, wherein the at least one ultrasonic receiver comprises a temperature sensor overlying an ultrasound absorber, and a hydrophone.

30. Imaging apparatus according to claim 1, comprising means for receiving a phase reference signal.

31. Imaging apparatus according to claim 1, wherein the at least one ultrasonic receiver comprises at least one ultrasonic receiver element which is sensitive to intensity of ultrasonic energy and also to acoustic pressure; the signal processing circuitry including a low frequency path and a high frequency path, wherein the low frequency path is operable to process a signal representative of the intensity of ultrasonic energy, and wherein the high frequency path is operable to process a signal representative of the acoustic pressure amplitude of the ultrasonic field.

32. Imaging apparatus according to claim 31, wherein the low frequency path has an upper frequency response of no more than 20 kHz and wherein the high frequency path has a lower frequency response of at least 20 kHz.

33. Imaging apparatus according to claim 31, wherein the ultrasonic receiver comprises two or more ultrasonic receiver elements.

34. Imaging apparatus according to claim 33, wherein the signal processing circuitry comprises two or more high frequency paths.

35. A method of imaging the spatial distribution of acoustic properties of a sample, comprising the steps of:
generating an ultrasonic field across an imaging area by means of at least one ultrasonic transmitter;
locating a sample in the ultrasonic field; sensing the intensity of the ultrasonic field generated by the transmitter or transmitters by means of at least one ultrasonic receiver which is sensitive to intensity of an ultrasonic field generated by the transmitter or transmitters, the at least one ultrasonic receiver comprising:
an ultrasonic absorber; and
a film which is divided into a plurality of separate elements comprising:
at least one pyroelectric ultrasonic sensing element in thermal communication with the ultrasonic absorber, which is sensitive to heating caused by the ultrasonic field and which has an accelerometer response; and
at least one pyroelectric compensation element which is substantially insensitive to heating caused by the ultrasonic field and which has an accelerometer response substantially similar to that of the at least one pyroelectric ultrasonic sensing element; and
processing a signal from the at least one ultrasonic receiver to derive therefrom an intensity measure and thus to derive a spatial distribution of the acoustic properties of said sample;
wherein the processing step further comprises removing the signal from the at least one pyroelectric compensation element from the signal from the at least one pyroelectric ultrasonic sensing element so as to compensate for the accelerometer response of the at least one pyroelectric ultrasonic sensing element.

36. An ultrasonic receiver array comprising:
a pyroelectric material; and
two or more poled regions of the pyroelectric material, wherein the poled regions are separated by a non-poled region.

37. An array according to claim 36, wherein the poled regions are arranged in a linear array and/or a two-dimensional array.

38. An array according to claim 36, wherein the poled regions are in thermal communication with an ultrasonic absorber.

39. An array according to claim 36, wherein the non-poled region is in thermal communication with an ultrasonic absorber.

40. An ultrasonic receiver comprising:
an ultrasonic absorber; and
a film which is divided into a plurality of separate elements comprising:
at least one pyroelectric ultrasonic sensing element in thermal communication with the ultrasonic absorber, which is sensitive to heating caused by an ultrasonic field and which has an accelerometer response; and
at least one pyroelectric compensation element which is substantially insensitive to heating caused by the ultrasonic field and which has an accelerometer response substantially similar to that of the at least one pyroelectric ultrasonic sensing element.

41. An ultrasonic receiver according to claim 40, wherein the pyroelectric compensation element overlies a cavity in the ultrasonic absorber.

42. An ultrasonic receiver according to claim 41, wherein the pyroelectric compensation element overlies: a passage through the ultrasonic absorber; or a material having a higher effective heat capacity than the ultrasonic absorber.

43. An ultrasonic receiver according to claim 40, comprising two or more ultrasonic sensing elements and/or two or more compensation sensing elements.

44. An ultrasonic receiver according to claim 40, comprising: a second ultrasonic absorber having a different thermal property and/or a different ultrasonic property to said ultrasonic absorber; a second pyroelectric ultrasonic sensing element in thermal communication with the second ultrasonic absorber.

45. An ultrasonic receiver according to claim 44, comprising two or more said ultrasonic sensing elements and/or two or more second ultrasonic sensing elements.

46. An ultrasonic receiver according to claim 40, wherein the pyroelectric compensation element has an overlying ultrasonic shield.

47. An ultrasonic receiver according to claim 46, wherein the ultrasonic shield is absorptive of ultrasonic energy or reflective to ultrasonic energy.

48. An ultrasonic receiver according to claim 46, comprising two or more first ultrasonic sensing elements and/or two or more second ultrasonic sensing elements.

* * * * *